United States Patent
Vande Pol et al.

[11] Patent Number: 6,016,570
[45] Date of Patent: Jan. 25, 2000

[54] POWDERFREE MEDICAL GLOVE

[75] Inventors: Mark Edward Vande Pol, Los Gatos; Kenneth Steven Horwege, Boulder Creek; Victoria Sanchez-Garcia, San Jose, all of Calif.

[73] Assignee: Maxxim Medical, Inc., Clearwater, Fla.

[21] Appl. No.: 09/075,747

[22] Filed: May 11, 1998

[51] Int. Cl.[7] .................................................. A41D 19/00
[52] U.S. Cl. ................................ 2/161.7; 2/168; 264/255
[58] Field of Search .......................... 2/160, 161.7, 161.3, 2/167, 168, 169; 264/255, 308

[56] References Cited

U.S. PATENT DOCUMENTS

| | | | |
|---|---|---|---|
| 2,120,406 | 6/1938 | Hansen | 2/161.7 |
| 3,813,695 | 6/1974 | Podell, Jr. et al. | |
| 3,883,899 | 5/1975 | Ganz | |
| 4,143,109 | 3/1979 | Stockum | |
| 4,310,928 | 1/1982 | Joung | |
| 4,329,312 | 5/1982 | Ganz | 2/168 |
| 4,947,487 | 8/1990 | Saffer et al. | |
| 5,088,125 | 2/1992 | Ansell et al. | |
| 5,180,605 | 1/1993 | Milner | 427/2 |
| 5,196,263 | 3/1993 | Melby et al. | 428/327 |
| 5,272,771 | 12/1993 | Ansell et al. | |
| 5,395,666 | 3/1995 | Brindle | 429/36.4 |
| 5,405,666 | 4/1995 | Brindle | |
| 5,438,709 | 8/1995 | Green et al. | 2/167 |
| 5,534,350 | 7/1996 | Liou | |
| 5,545,451 | 8/1996 | Huang et al. | |
| 5,644,798 | 7/1997 | Shah | 2/167 |
| 5,742,943 | 4/1998 | Chen | 2/168 |
| 5,792,531 | 8/1998 | Littleton et al. | 2/161.7 |
| 5,881,386 | 3/1999 | Horwege et al. | 2/161.7 |

OTHER PUBLICATIONS

Modern Plastics Encyclopedia, Fillers/Extenders, pp. 163, 166, 1982–83.

Primary Examiner—Diana Oleksa
Assistant Examiner—Katherine M. Moran
Attorney, Agent, or Firm—Kenneth M. Bush; Veal & Bush, LLC

[57] ABSTRACT

A powderfree medical film glove comprising an elastomer base layer having a sprayed, intermittent coating formed on the hand-contacting surface of the glove. The glove of the present invention improves donning by reducing intersurface tack, improves tactile sensory transmittance, and reduces unnecessary material consumption.

31 Claims, 1 Drawing Sheet

POWDERFREE MEDICAL GLOVE

FIELD OF THE INVENTION

The present invention relates to powderfree medical film gloves. More particularly, the present invention relates to a powderfree medical glove having a sprayed, intermittent coating to facilitate donning and tactile sensory transmittance.

BACKGROUND OF THE INVENTION

Medical film gloves are utilized by laboratory workers and physicians to reduce the incidence of contact transmission of various contaminants. Medical gloves should be relatively thin so that tactile sensation is not lost, however, the gloves must also be strong to resist rupture. Also, because the surfaces of film gloves tend to adhere to each other when packaged and to the user's hand while donning, the glove surfaces should have some form of lubricious property.

Conventional medical glove manufacturers typically utilize donning powders, such as corn starch or talc, over the surfaces of the glove to overcome the foregoing problems. Donning powders function as a lubricant by separating the glove surfaces to prevent self-adherence and to allow the glove surfaces to slide over a user's hand by reducing the friction between the glove and skin surfaces.

However, donning powders can also contaminate wounds, irritate skin, leave a residue on equipment and clothing, and mechanically interfere with some medical procedures. Powderfree gloves have been identified as a solution to many of the foregoing problems.

To render gloves powderfree, present methods utilize two basic friction reduction systems or a combination thereof. The first is replacing the powder with another lubricant and the second is imparting a contact-reducing texture to the hand-contacting surface of the glove. Commonly used lubricants include silicone oil, fatty acids, and surfactants. Lubricants, as well as gels and emollients, can have many of the same problems seen with powders. Thus, it is desirable to impart a lubricious feature to a glove without the use of lubricants or the like.

The present invention is directed to a powderfree glove having a contact-reducing texture formed on the hand-contacting surface of the glove. Present methods employed to impart this texture to a glove include hardening the glove surface to reduce friction with the user's skin and forming a textured coating over the base layer. However, problems encountered with hardened glove surfaces include reduction of mechanical performance, leading to greater incidence of cracks or breaks in the glove, and reduced sensitivity. In a multi-layered glove, the hardened layer can separate from adjoining layers during stripping from the glove former, donning by the user, or in use during flexure. This can result in tears in the adjoining layers.

More promising powderfree gloves comprise a textured coating formed over the base layer, such as the glove of U.S. Pat. No. 4,143,109, wherein Stockum teaches a coated glove having solid particles protruding from the coating to impart texture thereto, which reduces friction with the skin of the user during donning. However, the exposed solid particles can dislodge from the glove coating, thus failing the requirements of a powderfree glove. Another problem with coated gloves is conforming the relative elongation properties of the adjoining layers. Otherwise, the layers can separate or rupture during stripping, donning, or use. For example, because latex has a high degree of elasticity, any coating formed thereon often must have low modulus of elasticity. As used herein, the term "modulus" refers to how a material deforms under stress (force). A low modulus glove is softer and requires less force to deform whereas a relatively higher modulus glove is harder and requires more force to deform. In U.S. Pat. No. 5,534,350, Liou suggests that a minimum elongation of 500% is preferred to assure that the secondary coating will flex with the underlying latex glove. In the case of a vinyl glove, the glove will not have sufficient strength to overcome high stripping forces due to a high coefficient of friction. As a result, high stripping forces induce unacceptable distortion or complete failure of a vinyl product.

The principal method for applying coatings to gloves is through the process of dipping. Typically, a glove former is heated and dipped into a dip tank having the desired constituents (e.g. latex or vinyl, plasticizers, etc.) in liquid form, removed and drained to the desired film thickness, and heated in an oven to fuse (or vulcanize, cure, cross-link, etc.) the materials and form the glove. If subsequent layers are to be applied, the above process is repeated the number of times corresponding to the number of additional layers desired. In high speed manufacturing processes, or where the composition of the layers differs, additional dip tanks are typically required. For efficient manufacture, the steps must occur in rapid succession with the time for each step minimized. Once the final layer is formed, the glove former is cooled, a cuff can be formed on the glove, and the glove is stripped from the glove former and collected for packaging.

There have been suggestions in the prior art that coatings can be applied by spraying, after which, the glove former is heated in an oven to fuse (vulcanize, cure, cross-link, etc.) the sprayed coating. However, the prior art teaches the purpose of these spray coatings is to form a continuous film layer equivalent to that of a dipped product.

The prior art does not suggest using spray deposition methods to impart texture, nor does it suggest any advantage of a coating that is intermittent instead of continuous, which is the focus of the present invention.

SUMMARY OF THE PRESENT INVENTION

It is an object of the present invention to produce a powderfree medical film glove having a textured feature to facilitate donning by the user.

It is another object of the present invention to produce a powderfree glove having a textured feature to facilitate transmission of tactile sensation.

It is another object of the present invention to produce a powderfree glove having a textured feature to reduce intersurface tack arising in typical packaging and storage conditions, thus facilitating removal from the package and donning by the user.

It is another object of the present invention to produce a powderfree glove which substantially improves efficiency in manufacture, thus reducing manufacturing costs.

These and other objects of the present invention are accomplished with a powderfree medical glove comprising an elastomer base layer, preferably vinyl, having an intermittent coating formed thereon and applied by means of a controlled spray process. The sprayed coating is applied to the user-contacting surface of the glove, and preferably comprises a polyurethane binder, a hardener, a thickener, a surfactant, and a filler. The sprayed coating imparts a lubricious texture to the user-contacting surface so that it will slide over itself and over the user's skin to render the glove donnable without the need for powders. The basic method of forming the glove comprises the following steps:

1. The hand form is heated and dipped into an elastomeric plastisol bath.
2. The form is removed from the bath and allowed to drain to the desired weight and film thickness.
3. The form is heated in an oven to fuse the elastomer base layer of the glove.
4. The form and glove are partially cooled.
5. The intermittent coating is sprayed onto the surface of the glove in droplets of a controlled size distribution. The droplets air dry rapidly due to the residual heat of the glove so that subsequent droplets do not commingle. A unitary structure is thus formed on the surface of the mold.
6. A cuff is preferably formed using conventional automated equipment.
7. The glove is stripped from the mold surface by everting, forming a glove having a patient-contacting layer on an outside surface and a spray-textured, user-contacting surface on an inside surface.

Gloves of the present invention have improved flexibility, excellent elongation and strength properties, and a thickness which allows sufficient tactile sensitivity. Spraying allows the use of a coating that, because it is intermittent, can be formulated to be harder than would be allowable for a contiguous coating. The coating retains sufficient elongation and adhesion properties to meet current requirements for classification as a powderfree glove in end use.

The intermittent spray coating, reminiscent of cookies on a plate with some of them overlapping and the coated filler forming raised portions in a manner similar to chopped nuts, permits glove flexure between the dried coating spatters. A spray coating can be formulated and applied to reduce contact area due to spray texture. A spray coating can also be formulated to have more hardeners and fillers in amounts that would render prior art gloves too inflexible for use as a powderfree glove, while still providing excellent stripping and donning performance. The increased hardness allowed by the intermittent coating and the texture imparted by controlled spray application render the glove substantially free from self-adherence of the glove surfaces, thus facilitating donning of the glove by the user without the need for powder on the surfaces.

These and other objects and advantages of the invention will become apparent from the following detailed description of the preferred embodiment of the invention.

BRIEF DESCRIPTION OF THE DRAWINGS

A medical film glove embodying features of the present invention is described in the accompanying drawings which form a portion of this disclosure and wherein.

DETAILED DESCRIPTION OF THE PREFERRED EMBODIMENT

Figure 1:
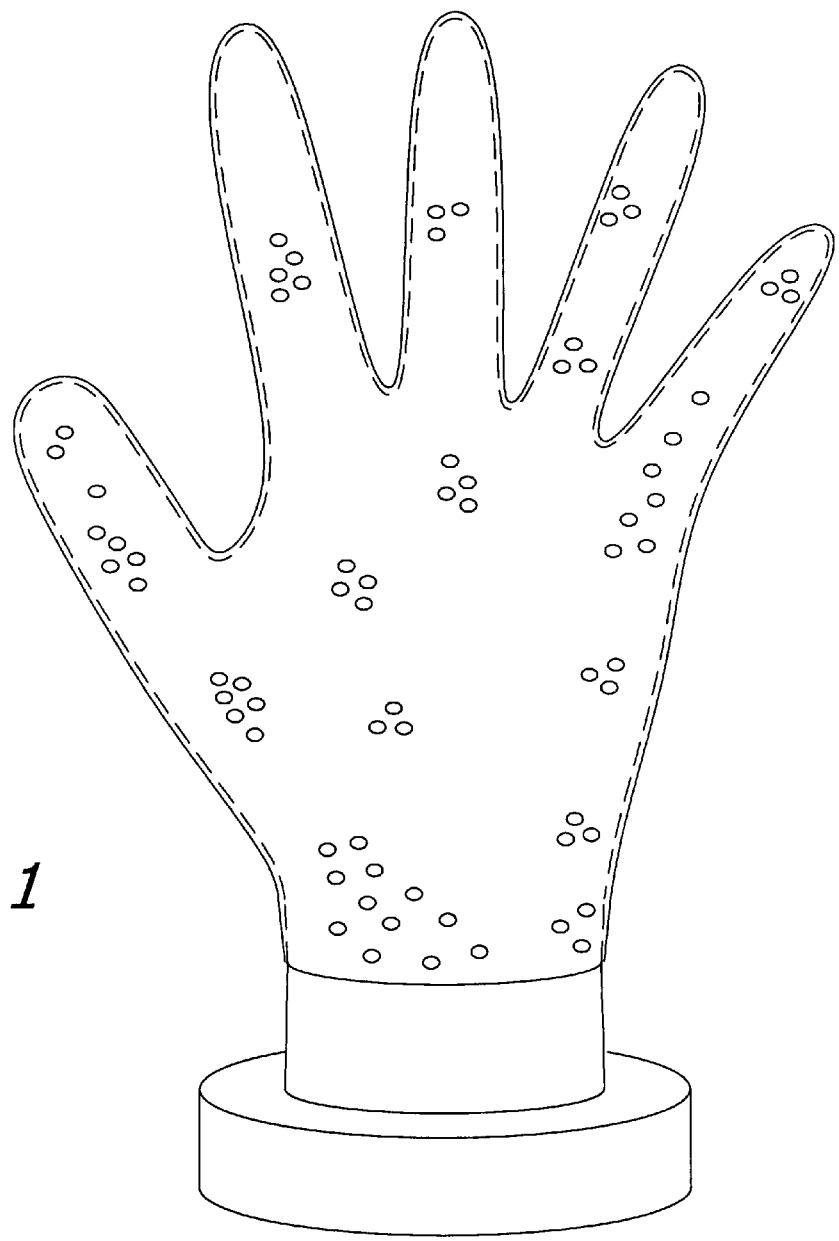
FIG. 1 is a perspective view of the glove according to the present invention on a glove former.

While this present invention is satisfied by embodiments in a range of forms and methods, there will be described herein examples of the preferred embodiment of the invention, with the understanding that the present disclosure is to be considered as exemplary of the principles of the invention and is not intended to limit the invention to the embodiments described. The following disclosure will describe a base layer comprising a vinyl polymer. However, the present invention is not limited to a vinyl base layer inasmuch as the intermittent layer can be deposited on any elastomer glove, including natural and synthetic rubbers.

The novel features of the present invention were discovered as a result of continued research of the technology disclosed in U.S. Pat. No. 5,881,386, incorporated herein by reference, by several of the same inventors. The '386 patent teaches that the presence of a slip agent (hardener) and a texturizing agent in a glove coating provides the surface of the user-contacting layer with a micro-roughness to substantially reduce the contact area between the user's skin and the glove surfaces, thereby allowing the glove to be donned without the powder required by current gloves. We found that more hardener improved the donnability of a glove having a continuous coating. However, a continuous harder coating reduces tactile sensation and is more likely to crack or rupture.

The present invention did not suffer from those shortcomings because the gaps within the intermittent coating allow the flexure of the glove without failure in coating adhesion. While the present invention uses much of the same chemical components as the '386 technology, they can be used in ranges that would not make a glove with acceptable flexibility, coating reliability, or sensitivity performance if such a formulation were applied in the form of a continuous coating. It has been found that the method employed by the present invention has allowed us to expand the ranges of acceptable chemicals considerably, particularly in the area of surface hardening components.

In the present invention, the selected thickener needs to have substantially no extensive viscosity and a high degree of pseudoplastic behavior (shear thinning). Extensive viscosity is the propensity of a fluid to form stings instead of breaking into discrete droplets, and is discussed in greater detail below. Commercial thickeners must be screened for both shear thinning and minimal extensive viscosity. Polyacrylic acid thickeners such as Carbopol® (BF Goodrich), a material which, although it exhibits an identical shear thinning curve as that of xanthan gum (the thickener in the present invention), has a nearly infinite extensive component. Xanthan gum, on the other hand, has an extensive viscosity component which is undetectable.

Sensitivity performance is more important in the finger areas of the glove because of the high density of tactile sensory receptors in the human fingers. An intermittent coating will allow the glove to flex without the added restraint of the coating membrane. The utilization of a sprayed material in such a way that the coating can be intermittent on critical sensory regions of the glove thus improves both the feel and comfort of the product. The utilization of a spray technique thus provides a compensatory benefit to vinyl glove sensitivity performance while simultaneously utilizing a harder coating material.

Materials that air dry can have poor adhesion to the base glove when sprayed unless the distribution of droplet sizes is controlled. Droplet mass is a function of the cube of the droplet radius while aerodynamic drag is a second order property. The higher cross-sectional area-to-volume ratio of an overspray droplet increases the effect of aerodynamic drag on the droplet and increases the flight time of the droplet from applicator to target. The smaller droplet also has a higher surface-to-volume ratio. This increases the rate at which it dries in flight. Both of these properties increase the risk that a small droplet will partially dry during flight and fail to adhere to the glove, thus forming thereon a loose particle. The presence of a high population of loose particulate fails to meet the criteria for a powderfree glove.

Sprayed, intermittent coatings improve packaging the product in such a way that it is easier to remove the glove from the box after long periods of storage under warehouse conditions. A continuous coating has residual intermaterial boundary stress in the finished glove that creates much of the compressive forces in packaging. Softer materials have the propensity to develop interior surface tack in response to these compressive forces and elevated temperatures imparted by packaging, casing, and storage in hot warehouses. The development of interior surface tack inhibits donning by the glove user. Spray coating processes can be designed to impart a surface texture that reduces the area of intersurface contact, resulting in lower intersurface tack.

Spraying properties are strongly affected by formulation. Texturizing agents and fillers, when used within the sprayed coating, harden the surface and improve the glove stripping performance during manufacture. These components, however, often settle and pack within production equipment. Uniformly suspending the texturizing agents is assisted by the selection of thickeners with rheological properties such that the coating formula can be efficiently applied with minimal overspray. These rheological properties are severe pseudoplasticity (shear thinning) and minimal extensive viscosity.

While pseudoplastic behavior is well understood, the extensive component of fluid viscosity is less so. Extensive viscosity, for the purpose of this application, is the propensity of a fluid to resist being broken into discrete droplets. Examples of the presence of extensive viscosity are sugars, such as cotton candy or honey. The presence of extensive viscosity exhibits an effect similar to the formation of cotton candy which would be totally unacceptable for a coating formulation for spray application. It is possible for two thickeners to have nearly identical shear-thinning behavior and totally divergent extensive properties.

In light of the foregoing, the glove of the present invention preferably comprises a base layer formed from plasticized polyvinyl chloride (PVC) or a PVC copolymer, and a sprayed, intermittent coating, adhered to the base layer, preferably comprising a polyurethane polymer as the principal binder, a surface hardener, a surfactant, fillers, and a thickener, wherein the intermittent coating becomes the user-contacting surface. For spray applications, the selection of the method of polyurethane polymerization and micelle size is also important to the prevention of excessive amounts of overspray. As a rule, the micelle size should be less than 10% of the minimum droplet size or else the formula will begin to manifest extensive viscosity. This is easily accomplished in the case of a dispersion polymerized polyurethane. The basic method of preparing the glove according to the present invention, comprises the following steps:

Step 1. A clean mold having the form of a human hand is heated to a temperature between about 70° C. to about 95° C. and dipped into a bath containing a polyvinyl chloride (PVC) plastisol, or a PVC copolymer with maleic or acrylic esters and the like as a plastisol, maintained at a temperature between about 35° C. to about 45° C.

The PVC plastisol preferably comprises a polyvinyl chloride dispersion resin having an intrinsic viscosity between about 0.7 to about 1.5 (ASTM D-1243 Method A); a plasticizer, preferably phthalate or adipate mono- or di-esters having between 7 to 10 carbon atom chains and blends thereof; a stabilizer component; and a pigment. The plastisol may also include viscosity modifiers, antifoam agents, and other components which are well known in the art. The mold residence time in the PVC bath, the solids content of the bath, and the temperature, all affect the thickness of the film formed. Preferably, the residence time is sufficient to allow the plastisol to form a film between about 0.03 mm to about 0.14 mm, depending upon the desired finished film thickness and intended application for the glove. The resin:plasticizer ratio is preferably between about 0.8:1 to about 1.2:1.

Step 2. The mold having the plastisol film on its surface is removed from the PVC bath and allowed to drain to the desired film thickness and weight.

Step 3. The mold having the plastisol film is then inserted into an oven to fuse the plastisol film. The oven conditions and residence time preferably are sufficient to raise the temperature of the film to between about 160° C. to about 195° C.

The term "fuse" as used herein is descriptive of the reaction of vinyl plastisol to form a solidified continuous layer and should not be considered limiting inasmuch as other materials can be used to form the base layer, wherein other terms such as vulcanize, cure, cross-link, or the like may be more appropriate. It is to be understood that the purpose of this step is to form a solidified continuous base layer.

Step 4. The mold having the fused film on its surface is cooled to between about 50° C. to about 120° C.

Step 5. The mold having the fused film on its surface is presented to a spray process capable of applying spray formula. The spray formulation preferably comprises a polyester polyurethane binder; a surface hardener to allow surface mobility and reduce tack; a filler to stiffen the dried matrix; a thickener to suspend the filler, regulate droplet formation, and assist with the formation of greater relief in texture; an antifoam agent; and a surface active agent to aid in wetting and promote adhesion of the binder to the vinyl film. The only material that must be present in the spray formula is the binder, but if this is the case, the binder must have hardness and wetting properties similar to that typically imparted by a hardener and surfactant, respectively. The polyester polyurethane, commercially available as an aqueous dispersion typically comprising between about 25% to about 40% solids, is present in the spray formula in an amount to form a dried coating having a dry weight percentage of polyester polyurethane between about 20% to about 100%, and most preferably between about 25% to about 60%. Other binders which should be efficacious include acrylic resin dispersions and various blends thereof.

The surface hardener, commercially available as an aqueous emulsion typically comprising between about 25% to about 40% solids, is present in the spray formula in an amount to form a dried coating having a dry weight percentage of hardener between about 20% to about 50%, and most preferably between about 25% to about 40%. The surface hardener allows the glove to be hot stripped from the surface of the mold. Suitable hardeners include various polyethylene and paraffin waxes, and other dispersed polymers with similar physical properties.

The filler preferably is a finely divided material having a particle size distribution preferably between about 1 to about 25 microns, and most preferably between about 3 to about 10 microns. If present, the filler is preferably in the spray formula in an amount to form a dried coating having a dry weight percentage of the filler less than about 25%. There is no preference in the chemical composition of the filler other than it be insoluble and dispersible. Examples of acceptable fillers include, but are not limited to, silicon dioxide, microcrystalline cellulose, calcium carbonate, diatomaceous earth, synthetic aluminosilicates, glass beads, silica, synthetic silicates, or any hard filler that is readily suspendable and most preferably close to a specific gravity of 1. Although the filler provides some texture, the primary texture arises from the sprayed spattered finish. Thus, based on our research, fillers can be completely omitted from the formula. However, this may require operation of the process with viscosity and droplet diameter ranges different from that for formulae with fillers.

The thickener, if present, preferably has no measurable extensive viscosity when dispersed in water, a high degree of pseudoplastic behavior (shear thinning), and rapid viscosity recovery properties. The thickener can be utilized to suspend the fillers, to serve as a formulary control element for control of droplets, and, after flight and impingement, to retain sufficient sphericity to enhance surface texture when dry. The correct amount of thickener will vary with the process parameters. If present, the thickener is preferably in the spray formula in an amount to form a dried coating having a dry weight percentage of the thickener less than about 7%. The preferred range of viscosity of the spray formula is between about 100 to about 2000 centipoise. The antifoam agent, if present, is preferably in the spray formula in an amount to form a dried coating having a dry weight percentage of the antifoam agent less than about 3%. The surfactant, if present, is preferably in the spray formula in an amount to form a dried coating having a dry weight percentage of the surfactant less than about 5%.

The mold is presented to the spray such that it can be coated with the spatters covering preferably between about 20% to about 90% of the glove surface to meet hot stripping requirements. For a softer feel in the finished product, the spatter finish coverage is preferably between about 40% to about 60% coverage by area, and most preferably in the fingers and thumb region of the glove. The spatter major diameter distribution is preferably between about 10 to about 300 microns and most preferably between about 20 to about 100 microns.

Once on the glove, the droplets should have a high degree of probability of being dry before being reimpinged or adjoined. This allows the spatters to remain unblended or wetted into a film, thus retaining spray texture properties.

Step 6. The unitary structure is maintained at a temperature between about 70° C. to about 90° C. and a cuff roll is formed on the unitary structure.

Step 7. The structure is then stripped and everted from the mold surface, forming a glove having a patient-contacting layer on an outside surface and a user-contacting finish on the inside surface.

Step 8. The finished gloves are counted and packaged for distribution.

Figure 2:
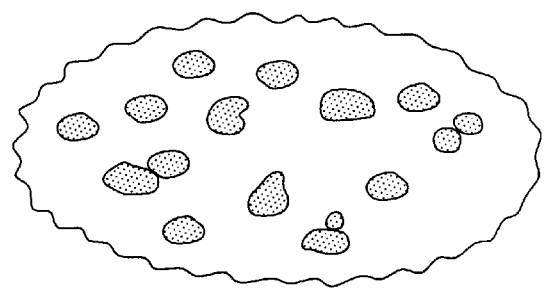
FIG. 2 is a magnified perspective view of the hand-contacting surface of the glove according to the present invention.

FIG. 1 illustrates the glove and intermittent coating of the present invention on a glove former and FIG. 2 illustrates the surface texture of the hand-contacting surface of the glove. For illustrative purposes, the dimensions of the droplets forming the intermittent coating have been exaggerated in the figures. Gloves prepared by the foregoing method have demonstrated reduced propensity to develop interior adhesion during prolonged storage and compression under warehouse conditions. This is attributable to two factors: the reduced intersurface contact area due to sprayed texture and the larger amount of surface hardeners allowed by the intermittent coating.

The mean diameter of the droplet size distribution can be adjusted while retaining a controlled droplet diameter distribution. In these cases the formula and the process parameters must be adjusted to achieve uniformity in the desired size range. For those cases in which the coating has no fillers, the distribution narrows and the mean diameter is smaller. The objectives of uniformity are: control of the rate of deposition for a relatively uniform texture, a minimum number of satellite droplets that might dry sufficiently to fail in adhesion, supply a frequency of void spaces such that the film can deflect without coating failure as desired, and minimize the propensity for the droplets to form a film. Given the objectives, the means to deliver these properties are well known in the art of paint coating applications and will not be discussed herein. An excellent resource relative to paint coating applications is *Atomization and Sprays* by Arthur Lefebvre (1989, Hemisphere Publishing Corp.).

Samples from commercially available powder free gloves were tested against the present invention for peak static coefficient of friction (COF) using ASTM Test Method D-1894, hereby incorporated by reference. The test apparatus (Kayeness D5095D) was set at 15.2 cm/minute with 190 grams on the sled. Table I gives the coefficient of friction and the standard deviation (inside parenthesis) at ambient temperature (between about 23° C. to about 30° C.) and at elevated temperature (between about 65° C. to about 77° C.). The results are from data run Apr. 16, 1997 on sprayed gloves made Mar. 19, 1997 and fifteen samples of dipped gloves made over a period of two years. For the purposes of this experiment, the temperature deviations within the ambient and within the elevated range were not significant.

TABLE I

| Ambient & Elevated Temperature Coefficient of Friction with (Standard Deviation) | | |
|---|---|---|
| Sample | 23–30° C. | 65–77° C. |
| Present Invention | 0.30 (0.10) | 0.41 (0.12) |
| Prior Art | 0.45 (0.09) | 0.38 (0.2) |

A lower coefficient of friction at elevated temperatures facilitates rapid stripping and everting of a glove from the mold. Results from our research confirmed that when the present invention is formulated with the same formulary constituents as the prior invention, it has, like the prior invention, a lower coefficient of friction at elevated temperatures when compared with other commercially available products tested. The hardener imparts the substantially lower coefficient of friction at elevated temperatures. The spatter finish of the present invention allows a higher percentage of hardener in the formula without coating failure than was possible with the prior, dipped invention. Unlike the prior invention, this higher percentage of hardener is accomplished without the loss of sensitivity.

A preferred embodiment of the present invention is a glove having physical properties as given below in Table II, but the present invention could be used with base glove films typically between about 0.035 mm to about 0.150 mm, depending on the particular applications. The gloves of the present invention provide strength and tactile sensitivity similar to popular powdered PVC gloves such as Sensi-Care® (Maxxim Medical, Inc.; Clearwater, Fla.) while providing the added benefit of powderfree donnability.

TABLE II

| Glove Properties | | |
|---|---|---|
| Site | Thickness | Strength |
| Cuff | 0.06 mm | Modulus at 200% between 500 and 900 psi; |
| Palm | 0.11 mm | Tensile strength between 1500 and 1700 psi. |
| Finger | 0.08 mm | Ultimate Elongation minimum about 500%. |

Following is a list of materials found to be suitable for use in the present invention. These agents and the following examples are intended to be exemplary and not limiting of the present invention.

| Trade Name | Chemical Type | Source |
|---|---|---|
| I. Polyvinyl Chloride (PVC): | | |
| a) Geon 1211 | PVC Dispersion Resin | GEON, Inc. (Cleveland, OH) |
| b) NV2 Formalon | PVC Dispersion Resin | Formosa Chemical (Livingston, NJ) |
| c) KV2 Formalon | PVC Dispersion Resin | Formosa Chemical (Livingston, NJ) |
| d) FPC 6337 | PVC Dispersion Resin | Oxychemical (Dallas, TX) |
| e) Oxy 80HC | PVC Dispersion Resin | Oxychemical (Dallas, TX) |
| f) Pliovic DR-600 | PVC Dispersion Resin | Goodyear Chemicals (Akron, OH) |
| Pliovic DR-602 | PVC Dispersion Resin | Goodyear Chemicals (Akron, OH) |
| Pliovic DR-652 | PVC Dispersion Resin | Goodyear Chemicals (Akron, OH) |
| g) Pliovic MC-85 | PVC Copolymer Resin | Goodyear Chemicals (Akron, OH) |
| h) VC 1070, VC 1071 | PVC Dispersion Resin | Borden Chemical (Geismar, LA) |
| i) EH-71 | PVC Dispersion Resin | Georgia Gulf (Plaquemine, LA) |
| II. Plasticizers for PVC: | | |
| a) Santicizer 711 | Phthalate Ester | Monsanto (St. Louis, MO) |
| b) Jayflex DOP | Phthalate Ester | Exxon (Houston, TX) |
| c) Jayflex 77 | Phthalate Ester | Exxon (Houston, TX) |
| d) Jayflex DINP | Phthalate Ester | Exxon (Houston, TX) |
| e) Kodaflex DOTP | Phthalate Ester | Eastman (Kingsport, TN) |
| f) Kodaflex DOA | Adipate Ester | Eastman (Kingsport, TN) |
| g) Jayflex DINA | Adipate Ester | Exxon (Houston, TX) |
| III. Stabilizers: | | |
| a) Drapex 4.4 | Epoxidized Tall Oil | Witco (NY, NY) |
| b) Drapex 6.8 | Epoxidized Soybean Oil | Witco (NY, NY) |
| c) Interstab CZL-717 | Transition Metal Soap | Akzo (Dobbs Ferry, NY) |
| d) Interstab LT-4468 | Transition Metal Soap | Akzo (Dobbs Ferry, NY) |
| IV. Viscosity Modifiers: | | |
| a) Jayflex 215 | Paraffin Oil | Exxon (Houston, TX) |
| b) Deplastol | Polyethylene Glycol | Henkel |
| V. Fillers: | | |
| a) Atomite | Calcium carbonate | ECC America (Sylacauga, AL) |
| b) Microcal 120 | Calcium carbonate | ECC America (Sylacauga, AL) |
| c) Duramite | Calcium carbonate | ECC America (Sylacauga, AL) |
| d) Celite | Diatomaceous earth | Hill Bros. Chem. (Orange, CA) |
| e) Zeothix, Zeolite | Aluminosilicates | J. M. Huber (Haver de Grace, MI) |
| f) Sipemate | Silicate | Degussa (Ridgefield Park, NJ) |
| g) Lattice NT006 | Microcrystalline Cellulose | FMC (Phila. PA) |
| h) Avacel PH105 | Microcrystalline Cellulose | FMC (Phila. PA) |
| VI. Surface Hardeners: | | |
| a) Polyemulsion OA3N30 | Oxidized Polyethylene Emulsion | Chemical Corp. of Amer. (E. Rutherford, NJ) |
| b) Polyethylene OA3 | Oxidized Polyethylene Emulsion | Michelman, Inc. (Cincinnati, OH) |
| c) Jonwax 22 | Microcrystalline Wax Dispersion | SC Johnson |
| d) Jonwax 26 | Polyethylene Wax Emulsion | SC Johnson |
| e) Jonwax 120 | Polyethylene Paraffin Emulsion | SC Johnson |
| f) Polygen PE | Polyethylene Wax Dispersion | BASF |
| g) Polywax E1040 | Emulsifiable Low Molecular Weight Polyethylene | Petrolite |
| h) EPDM 603A | Ethylene Propylene Diene Polymer | BF Goodrich |
| i) Acrylic Elastomers | Acrylic Dispersions | Various suppliers |
| j) (Metallocene) | Polyolefin Elastomers | Various suppliers |
| k) BASF WE-1 | Oxidized Polyethylene Emulsion | BASF |
| VII. Thickeners: | | |
| a) Keltrol RD | Xanthan Gum | Kelco, Inc. (San Diego, CA) |
| Kelzan S | Xanthan Gum | Kelco, Inc. (San Diego, CA) |
| Kelzan | Xanthan Gum | Kelco, Inc. (San Diego, CA) |
| b) Kelgin HV | Sodium Algenate | Kelco, Inc. (San Diego, CA) |
| Keltex | Sodium Algenate | Kelco, Inc. (San Diego, CA) |
| Kelvis | Sodium Algenate | Kelco, Inc. (San Diego, CA) |
| c) Kelmar | Potassium Algenate | Kelco, Inc. (San Diego, CA) |
| VIII. Binder: | | |
| a) Solucote 10511-3-35 | Polyester Polyurethane Dispersion | Soluol Chem. Co. (West Warwick, RI) |
| b) Impranil DLN | Polyester Polyurethane Dispersion | Miles, Inc. (El Toro, CA) |
| c) Bayhydrol LS2033 | Polyester Polyurethane Dispersion | Miles, Inc. (El Toro, CA) |
| d) Witcobond 506 | Polyester Polyurethane Dispersion | Witco (NY, NY) |

-continued

| Trade Name | Chemical Type | Source |
| --- | --- | --- |
| e) Witcobond 781 | Polyester Polyurethane Dispersion | Witco (NY, NY) |
| f) Daotan VTW 1265 | Polyester Polyurethane Dispersion | Vianova Resins |
| IX. Antifoam Agents: | | |
| a) Bubble Breaker 625 | Alkoxylate Fatty Acid | Witco (Houston, TX) |
| b) Balab 625 | Alkoxylate Fatty Acid | Witco |
| c) Foam Control Agent A76 | Proprietary | Ashland Chemical |
| d) Foamaster PC | Proprietary | Henkel |
| e) Foamkill 649 | Proprietary | Crucible |
| X. Surface Active Agents: | | |
| a) Antarox LF330 | Modified Aliphatic Polyether | Rhone Poulenc (Cranbury, NJ) |
| b) BYK-345 | Silicone Polymer Surfactant | BYK Inc. (Wallingford, CT) |

While the inventors herein have developed embodiments of the invention without fillers, the following examples without fillers are prophetic in nature, but should be viable based on our research.

EXAMPLE 1

A clean mold having the form of a hand for an outside surface is heated to a temperature between about 70° C. to about 95° C. and dipped into a polyvinyl chloride (PVC) plastisol bath at a temperature between about 35° C. to about 45° C. to form a PVC plastisol film on its surface. The mold having the film on its surface is removed from the bath, allowed to drain, then heated in an oven to raise the temperature of the film on the mold surface to between about 160° C. to about 195° C., forming a fused film with an average thickness of about 0.08 mm. The mold is cooled to between about 90° C. to about 85° C. The mold having the film on its surface is presented to a spray process that deposits a lognormal distribution of spray droplets with a 4ρ region (95% confidence) of droplet diameters ranging from about 15 microns to about 100 microns in major droplet diameter. The formula is constituted of an aqueous emulsion including a polyurethane dispersion, a surface hardener, and a thickener to form a spatter finish on the PVC layer. The coating air dries on the film to form a unitary structure. A cuff is then formed on the unitary structure between about 80° C. to about 70° C. The unitary structure is further cooled to about 60° C. and is stripped and everted to form a glove.

Composition of Formulae for Example 1:

| Materials-Plastisol Dip | Parts per 100 (weight/weight) |
| --- | --- |
| KV2 Formalon | 8.2 |
| NV2 Formolon | 42.3 |
| Jayflex DINP | 43.4 |
| Jayflex 215 | 1.9 |
| Drapex 4.4 | 1.5 |
| Interstab LT-4468 | 2.0 |
| Deplastol | 0.4 |
| Pigment | 0.3 |

| Materials-Spray Formula | Parts per 100 (weight/weight) |
| --- | --- |
| Witcobond 506 | 15.0 |
| Jonwax 26 | 10.0 |
| Keltrol RD | 0.5 |
| Bubble Breaker 625 | 0.1 |
| Antarox LF 330 | 0.5 |
| Water | Q.S.100 |

EXAMPLE 2

A first layer PVC glove is formed and fused in like manner to that in Example 1. The film is cooled to between about 105° C. to about 95° C. The mold having the film on its surface is presented to a spray process that deposits a lognormal distribution of spray droplets with a 4ρ region of droplet diameters ranging from about 30 microns to about 150 microns in major droplet diameter. The formula is constituted of an aqueous emulsion including a polyurethane dispersion, a surface hardener, a filler, and a thickener to form a spatter finish on the PVC layer. The coating air dries on the film to form a unitary structure. A cuff is then formed on the unitary structure between about 85° C. to about 75° C. The unitary structure is farther cooled to about 70° C. and is stripped and everted to form a glove.

Composition of Formulae for Example 2:

| Materials-Plastisol Dip | Parts per 100 (weight/weight) |
| --- | --- |
| Oxy 80 HC | 46.3 |
| Jayflex 215 | 1.3 |
| Jayflex 77 | 48.0 |
| Drapex 4.4 | 1.7 |
| Interstab CZL-717 | 1.7 |
| Deplastol | 0.5 |
| Pigment | 0.5 |

| Materials-Spray Formula | Parts per 100 (weight/weight) |
| --- | --- |
| Solucote 10511-3-35 | 15.0 |
| Polyemulsion OA3-N30 | 15.0 |
| Atomite | 4.0 |
| Keltrol RD | 1.0 |
| Antarox LF330 | 0.5 |
| Water | Q.S. 100 |

EXAMPLE 3

A first layer PVC glove is formed and fused in like manner to that of Example 1. The film is cooled to between about 120° C. to about 110° C. The mold having the film on its surface is presented to a spray process that deposits a lognormal distribution of spray droplets with a 4ρ region of droplet diameters ranging from about 30 microns to about 150 microns in major droplet diameter. The formula is constituted of an aqueous emulsion including a polyurethane dispersion, a surface hardener, a filler, and a thickener to form a spatter finish on the PVC layer. The coating air dries to form a unitary structure. A cuff is then formed on the unitary structure at 100° C. to about 80° C. The film is air cooled to approximately 75° C. and the structure is stripped and everted to form a glove.

Composition of Formulae for Example 3:

| Materials-Plastisol Dip | Parts per 100 (weight/weight) |
| --- | --- |
| NV2 Formalon | 36.0 |
| Pliovic MC-85 copolymer | 12.1 |
| Kodaflex DOTP | 44.0 |
| Kodaflex DOA | 4.3 |
| Interstab LT-4468 | 1.5 |
| Jayflex 215 | 1.5 |
| Pigment | 0.7 |

| Materials-Spray Formula | Parts per 100 (weight/weight) |
| --- | --- |
| Bayhydrol LS 2033 | 15.9 |
| Polyethylene OA3 | 15.9 |
| BYK-345 | 0.4 |
| Lattice NT006 | 1.0 |
| Kelzan | 2.0 |
| Foamaster PC | 0.2 |
| Water | Q.S. 100 |

EXAMPLE 4

A first layer PVC glove is formed and fused in like manner to that of Example 1. A cuff is then formed on the unitary structure between about 90° C. to about 70° C. The film is cooled to between about 80° C. to about 65° C. and the mold having the film on its surface is presented to a spray process. The spray process deposits a lognormal distribution of spray droplets with a 4ρ region of droplet diameters ranging from about 10 microns to about 90 microns in major droplet diameter. The formula is constituted of an aqueous emulsion including a polyurethane dispersion, a surface hardener, a filler, and a thickener to form a spatter finish on the PVC layer. The coating air dries to form a unitary structure and the structure is stripped at 40° C. and everted to form a glove.

| Composition of Formulae for Example 4: | |
| --- | --- |
| Materials-Plastisol Dip | Parts per 100 (weight/weight) |
| Oxy 80 HC | 49.0 |
| Jayflex DINP | 35.0 |
| Jayflex DINA | 11.0 |
| Drapex 6.8 | 2.0 |
| Interstab CZL-717 | 2.0 |
| Deplastol | 0.5 |
| Pigment | 0.5 |

| Materials-Spray Formula | Parts per 100 (weight/weight) |
| --- | --- |
| Solucote 105II-3-35 | 20.0 |
| Jonwax 120 | 16.0 |
| Kelzan S | 1.0 |
| BYK 345 | 0.4 |
| Water | Q.S. 100 |

It is to be understood that the form of the invention shown is a preferred embodiment thereof and that various changes and modifications may be made therein without departing from the spirit of the invention or scope as defined in the following claims.

Having set forth the nature of the invention, what is claimed is:

1. An elastomer film glove comprising a hand-contacting surface having a textured coating wherein said textured coating comprises a sprayed, intermittent coating of dried spray formula adhered to said hand-contacting surface, said intermittent coating comprising a plurality of raised droplets of said dried spray formula.

2. A glove according to claim 1, wherein said elastomer comprises polyvinyl chloride.

3. A glove according to claim 1, wherein said elastomer is selected from the group consisting of natural and synthetic rubbers.

4. A glove according to claim 1, wherein said intermittent coating covers from about 20% to about 90% of the surface area of said hand-contacting surface.

5. A glove according to claim 1, wherein said intermittent coating covers from about 40% to about 60% of the surface area of said hand-contacting surface.

6. A glove according to claim 1, wherein said spray formula comprises a binder selected from the group consisting of polyurethanes, acrylic resins, and derivatives thereof.

7. A glove according to claim 6, wherein said binder is polyester polyurethane.

8. A glove according to claim 6, wherein said spray formula further comprises a hardener.

9. A glove according to claim 8, wherein said hardener is selected from the group consisting of polyethylene and paraffin waxes.

10. A glove according to claim 8, wherein said hardener is an oxidized polyethylene.

11. A glove according to claim 6, wherein said spray formula further comprises a thickener having substantially no extensive viscosity.

12. A glove according to claim 6, wherein said spray formula further comprises a filler.

13. A glove according to claim 12, wherein said filler comprises a particle size distribution between about 1 to about 25 microns.

14. A glove according to claim 12, wherein said filler comprises a particle size distribution between about 3 to about 10 microns.

15. A glove according to claim 12, wherein said filler is selected from the group consisting of silicon dioxide, microcrystalline cellulose, calcium carbonate, diatomaceous earth, synthetic aluminosilicates, glass beads, silica and synthetic silicates.

16. A glove according to claim 6, wherein said spray formula further comprises a surfactant.

17. A glove according to claim 6, wherein said spray formula further comprises an antifoam agent.

18. An elastomer film glove comprising a hand-contacting surface having a sprayed, intermittent coating of dried spray formula adhered thereto, said intermittent coating comprising a plurality of droplets of said dried spray formula, wherein the diameter of said droplets ranges from about 10 microns to about 300 microns.

19. An elastomer film glove comprising a hand-contacting surface having a sprayed, intermittent coating of dried spray formula adhered thereto, said intermittent coating comprising a plurality of droplets of said dried spray formula, wherein the diameter of said droplets ranges from about 20 microns to about 100 microns.

20. A powderfree film glove, comprising a base layer having a thickness between about 0.035 mm to about 0.150 mm selected from the group consisting of elastomeric polymers, wherein a user-contacting surface of said base layer has an intermittent textured coating sprayed thereon and unitized thereto to form a unitary glove, said intermittent coating comprising a plurality of raised droplets of dried spray formula dispersed over said base layer such that said base layer is capable of flexion without disrupting adhesion of said intermittent coating to said base layer, said spray formula comprising a hardener to increase tactile sensitivity of a wearer and to permit donning of said glove without powders or other lubricants.

21. A polyvinyl film glove comprising a hand-contacting surface having a textured coating wherein said textured coating comprises an intermittent coating of dried spray formula adhered to said hand-contacting surface, said intermittent coating comprising a plurality of raised droplets of said dried spray formula.

22. A glove according to claim 21, wherein said intermittent coating covers from about 20% to about 90% of the surface area of said hand-contacting surface.

23. A glove according to claim 21, wherein said spray formula comprises a polyester polyurethane binder.

24. A glove according to claim 23, wherein said spray formula further comprises an oxidized polyethylene hardener.

25. A glove according to claim 23, wherein said spray formula further comprises a thickener having substantially no extensive viscosity.

26. A glove according to claim 23, wherein said spray formula further comprises a filler, said filler being insoluble in said spray formula.

27. A glove according to claim 24, wherein said spray formula farther comprises a surfactant.

28. A polyvinyl film glove comprising a hand-contacting surface having an intermittent coating of dried spray formula adhered thereto, said intermittent coating comprising a plurality of droplets of said dried spray formula, wherein the diameter of said droplets ranges from about 10 microns to about 300 microns.

29. A polyvinyl film glove comprising a hand-contacting surface having an intermittent coating of dried spray formula adhered thereto, said intermittent coating comprising a plurality of droplets of said dried spray formula, wherein said spray formula comprises a polyester polyurethane binder and a filler, wherein said filler is insoluble in said spray formula and said filler has a specific gravity of about 1.

30. An elastomer film glove comprising a hand-contacting surface having a sprayed, intermittent coating of dried spray formula adhered thereto, said intermittent coating comprising a plurality of droplets of said dried spray formula, wherein said spray formula comprises a filler having a specific gravity of about 1.

31. An elastomer film glove comprising a hand-contacting surface having a sprayed, intermittent coating of dried spray formula adhered thereto, said intermittent coating comprising a plurality of droplets of said dried spray formula, wherein said spray formula comprises a thickener having substantially no extensive viscosity.

* * * * *